United States Patent [19]

Miyasaka et al.

[11] Patent Number: 5,154,808

[45] Date of Patent: * Oct. 13, 1992

[54] FUNCTIONAL ORGANIC THIN FILM AND PROCESS FOR PRODUCING THE SAME

[75] Inventors: Tsutomu Miyasaka; Koichi Koyama, both of Kanagawa, Japan

[73] Assignee: Fuji Photo Film Co., Ltd., Kanagawa, Japan

[*] Notice: The portion of the term of this patent subsequent to Jan. 22, 2008 has been disclaimed.

[21] Appl. No.: 715,313

[22] Filed: Jun. 12, 1991

Related U.S. Application Data

[63] Continuation of Ser. No. 211,502, Jun. 24, 1988, abandoned.

[30] Foreign Application Priority Data

Jun. 26, 1987 [JP] Japan ................................. 62-158996

[51] Int. Cl.$^5$ ............................ B32B 9/04; B05D 3/06
[52] U.S. Cl. ............................ 204/157.15; 204/157.6; 204/157.64; 204/157.81; 427/554; 427/553; 435/177; 435/180
[58] Field of Search ........... 204/157.15, 157.6, 157.64, 204/157.81; 427/53.1, 54.1; 435/177, 180

[56] References Cited

U.S. PATENT DOCUMENTS

| | | | |
|---|---|---|---|
| 3,959,078 | 5/1976 | Guire | 435/179 |
| 4,007,089 | 2/1977 | Smith, III | 522/87 |
| 4,269,941 | 5/1981 | Ichimura | 522/78 |
| 4,451,568 | 5/1984 | Schneider et al. | 522/78 |
| 4,597,999 | 7/1986 | Lingwood | 427/54.1 |
| 4,716,122 | 12/1987 | Scheeters | 436/532 |
| 4,973,493 | 11/1990 | Guire | 435/181 |
| 4,979,959 | 12/1990 | Guire | 435/176 |
| 4,987,032 | 1/1991 | Miyasaka et al. | 204/157.6 |

FOREIGN PATENT DOCUMENTS 82093 7/1981 Japan .
61-153559 7/1986 Japan .

Primary Examiner—John Niebling
Assistant Examiner—David G. Ryser
Attorney, Agent, or Firm—Sughrue, Mion, Zinn, Macpeak & Seas

[57] ABSTRACT

A functional organic thin film comprising a water-insoluble organic thin film comprising at least one of a nitrene group and a carbene group and a bioactive protein chemically bound to said at least one of a nitrene group and a carbene group; and the method for producing the same.

13 Claims, No Drawings

FUNCTIONAL ORGANIC THIN FILM AND PROCESS FOR PRODUCING THE SAME

This is a continuation of application Ser. No. 211,502, filed Jun. 24, 1988, now abandoned.

FIELD OF THE INVENTION

The present invention relates to a functional organic thin film obtained by a binding reaction between an organic molecule having a photochemically active functional group and a bioactive protein.

BACKGROUND OF THE INVENTION

Techniques for immobilizing bioactive proteins such as enzymes, antigens or antibodies onto an insoluble carrier such as a high molecular weight compound have been widely been studied as techniques for forming a bioreactor intended to separate, synthesize or decompose biosubstances. In recent years, however, utilization of the above-described immobilizing techniques for forming biosensors by immobilizing bioactive proteins onto the surface of a base of microelectrode or other transducer has been desired in addition to their utilization for forming bioreactors. For this purpose, it is generally required that the thin film functioning as carrier or support be thin and strong; that the immobilization be strong; that activity of the bioactive protein be kept at a high level; and that the immobilization amount be uniform. Further, in order to improve the response properties of the sensor, it is required to immobilize the bioactive protein onto a limited portion of a microtransducer at a high density.

In conventional enzyme-immobilizing processes, polymer beads or the like are generally used as carriers. However, few of them can form thin films showing good adhesion to a base due to their poor thin film-forming ability, because of their high molecular weights, or due to their swelling properties. In addition, since immobilization of enzymes is generally based on thermal reaction such as formation of amido bonds or Schiff bases, immobilization is difficult to control with respect to position or area.

JP-A-61-153559 (the term "JP-A" as used herein means an "unexamined published Japanese patent application") discloses a process of immobilizing a bioactive protein onto desired portions of a thin film formed on a sensor base by forming a pattern of a thin film containing the bioactive protein. In this process, a water-soluble diazide type light-sensitive polymer is used as a carrier, and a technique of hardening the polymer by irradiation with light to thereby immobilize enzyme dispersed in the polymer is employed.

This process is effective for the purpose of forming a pattern since the light-irradiating technique is employed for immobilization. However, since enzyme molecules are buried in the hardened resin, there is a considerable risk of losing enzyme activity. Further, highly active enzyme molecules located on the resin surface are considered to be easily desorbed.

JP-A-56-82093 discloses a process of dispersing an enzyme in an azido group-containing polymer and irradiating it with light to thereby immobilize the enzyme in the polymer matrix. In this process, however, water-soluble polymers (e.g., polyvinyl alcohol) are used to disperse the enzyme, and hence the light-crosslinked product has swelling properties, which makes it unsuited for forming a stable, insoluble film. In addition, because the enzyme molecules are buried in the polymer matrix as in the above described process, the enzyme activity is liable to be depressed.

It is important to solve these problems in order to form an organic thin film showing the high efficiency required for use as sensor, i.e., being strongly bound to a base and having a thin film thickness and a high immobilization density.

SUMMARY OF THE INVENTION

It is, therefore, an object of the present invention to provide a process for effectively immobilizing a bioactive protein onto an insoluble organic thin film by irradiation with light and to provide a highly active, functional organic thin film formed by the above-described process.

Another object of the present invention is to provide a functional film for use as a biosensor, which has formed on a base an organic thin film of sufficiently thin thickness that is difficult to delaminate therefrom.

A further object of the present invention is to provide a process for forming a functional organic thin film while controlling immobilization positions of bioactive proteins such as enzyme utilizing irradiation with light.

These and other objects of the present invention will become apparent from the following description.

It has now been found that the above-described and other objects of the present invention are attained by a functional organic thin film comprising a water-insoluble organic thin film comprising a nitrene group or a carbene group with a bioactive protein chemically bound to the nitrene group or the carbene group; and a functional organic thin film material comprising a support having provided thereon the functional organic thin film.

DETAILED DESCRIPTION OF THE INVENTION

The functional organic thin film material of the present invention can be produced by a method comprising the steps of:

(a) providing on a support a water-insoluble organic thin film containing at least a nitrene precursor or a carbene precursor; and (b) exposing the organic thin film in the presence of a bioactive protein to light.

The functional organic thin film of the present invention constitutes a base (support), a water-insoluble organic thin film coated thereon, and a layer of bioactive protein immobilized on the organic thin film through chemical bonds.

The process for forming this functional organic thin film includes the steps of (1) forming a water-insoluble organic thin film on the base surface; and (2) immobilizing a bioactive protein onto the surface of the organic thin film utilizing light, with the water-insoluble organic thin film containing a nitrene or carbene precursor, preferably a substantially water-insoluble precursor.

The nitrene or carbene precursors used in the present invention are organic compounds capable of producing a functional group having an active radical (e.g., nitrene or carbene) upon absorption of visible light or ultraviolet rays. They are light-sensitive compounds capable of chemically binding a bioactive protein through reaction with the active radical.

Typical examples of these precursors include azido and diazido compounds (precursors of nitrene) and α-diazidoketones and aryldiazirine compounds (precursors of carbene). These compounds respond to visible light or ultraviolet light to produce nitrene or carbene. Nitrene and carbene are extremely reactive intermediates known to effectively react with organic substances such as biopolymers. In addition, the production of nitrene or carbene from these precursors can be easily controlled because they can be activated by irradiation with light. Thus, the time for initiating the reaction can be freely selected.

This advantage has been widely utilized as a photoaffinitive labeling method useful for clarifying complicated functions of biopolymers. Studies on the photoaffinitive labeling method are reviewed in detail in H. Bayley and J. R. Knowles; *Methods for Enzymology*, vol. 46, pp. 69 to 114 (Academie Press, NY, 1977).

Preferred examples of the precursors to be used in the present invention are illustrated below, however, these are not to be construed as limiting the scope of the present invention.

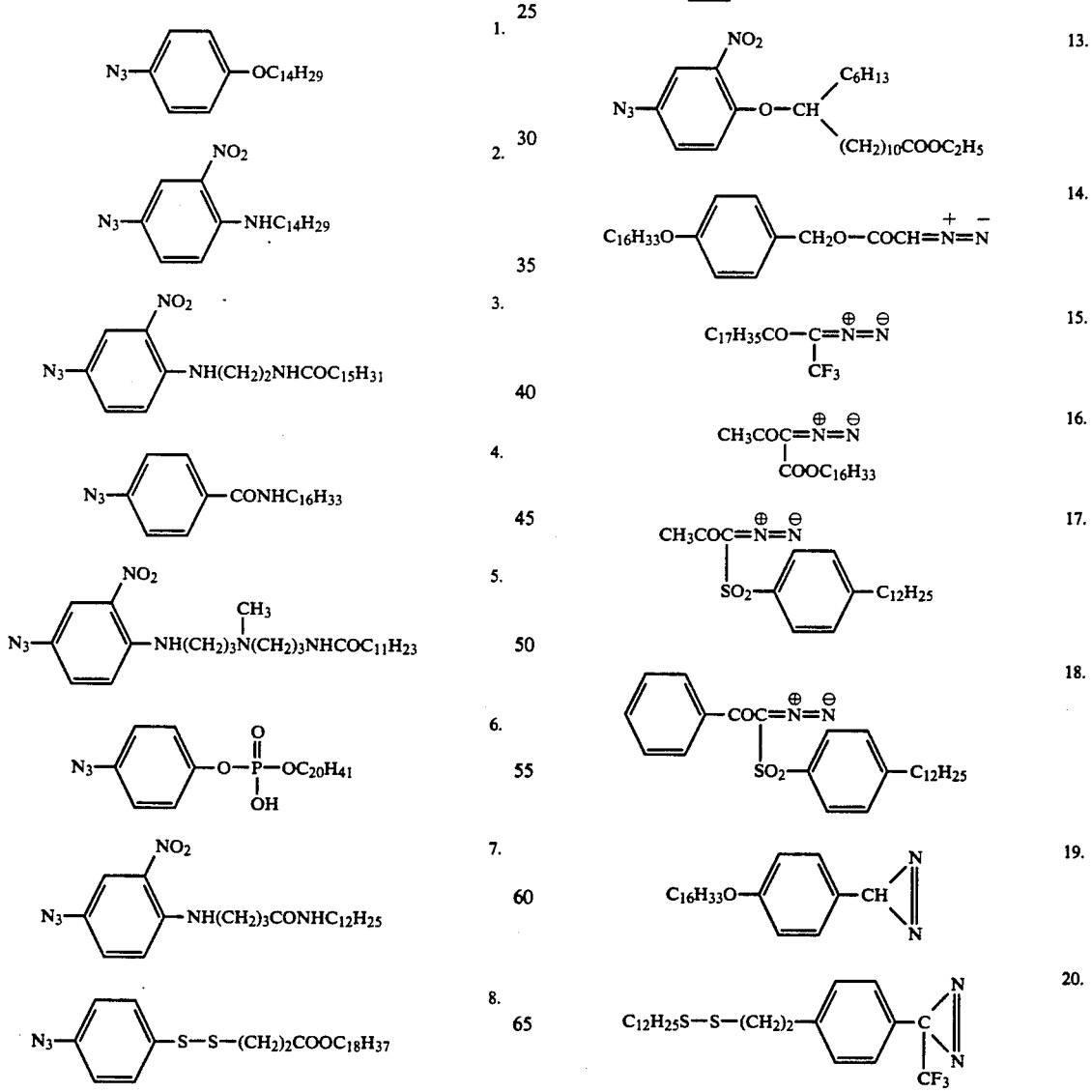

21.

[structure: C12H25O-C6H4-C(CF3) diazirine]

22.

$$CF_3C\overset{\oplus}{=}\overset{\ominus}{N=N}$$
$$\phantom{CF_3C=}COOC_{18}H_{37}$$

23.

$$CF_3C\overset{\oplus}{=}\overset{\ominus}{N=N}$$
$$\phantom{CF_3C=}COSCH_2CH_2COOC_{12}H_{25}$$

24.

[structure: C12H25O(CH2)2-C6H4-C(CF3) diazirine]

25.

[structure: C12H25-C6H4-SO2O(CH2)2-C6H4-C(CF3) diazirine]

26.

[structure: CH3OC(O)(CH2)10O-C6H4-C(CF3) diaziridine with H on N]

27.

[structure: C12H25O-C6H4-C(CF3) diazirine, meta]

28.

$$C_{16}H_{33}OOCC\overset{\oplus}{=}\overset{\ominus}{N=N}$$
$$\phantom{C_{16}H_{33}OOCC=}COOC_2H_5$$

29.

[structure: benzophenone with 4-NHCOC12H25 substituent]

30.

[structure: octalinone with C18H37 group]

31.

[structure: O=C(C2H5)-CH=CH-NH-C12H25]

32.

[structure: hydantoin-like ring with I and C18H37]

33.

[structure: C17H35CO-O-phenyl]

34.

[structure: C17H35CO-O-biphenyl]

35.

[structure: benzophenone with OC16H33 substituent]

Among the above compounds, those capable of immobilizing bioactive proteins when irradiated with visible light are preferred. Specifically, Compounds 2, 3, 5, 7, 9, 10, 12 and 13 are preferably used in the present invention.

The nitrene or carbene precursors used in the present invention may be easily synthesized by conventional manner known in organic chemistry. For example, with the nitrene precursors, aromatic azide compounds may be easily synthesized by diazotizing an aromatic amine and treating the product with sodium azide. Introduction of a hydrophobic group may be attained by utilizing, for example, an aromatic substitution reaction with an alkylamine, an amide-forming reaction or an etherification reaction with an alkyl halide.

Synthesizing processes are described below for typical precursors of the present invention.

SYNTHESIS EXAMPLE 1

Compound 5 was synthesized according to the following scheme:

[scheme: 4-fluoro-3-nitroaniline (I) → 1-fluoro-2-nitro-4-azidobenzene (II) → ]

[scheme continuation: reaction with HN(CH2)3N(CH3)(CH2)3NH2 giving compound (III) with NO2 and N3 substituents →]

-continued

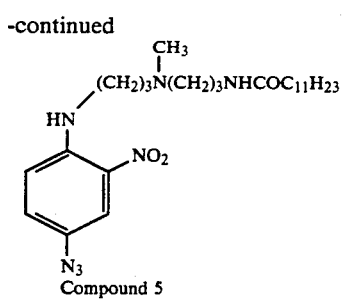

Compound 5

Synthesis of intermediate (II):

10 g of 4-fluoro-3-nitroaniline (I) was dissolved in 100 ml of hot conc. hydrochloric acid. This solution was cooled to $-15°$ to $-20°$ C., and a solution of 4.8 g of sodium nitrite in 10 ml of water was gradually dropwise added thereto at a temperature of not higher than $-15°$ C. Then, a solution of 4.4 g of sodium diazide in 16 ml of water was gradually added thereto at a temperature of not higher than $-15°$ C. After completion of the addition, the solution was stirred for about 30 minutes and, after generation of a nitrogen gas completely stopped, crystals precipitated were collected by filtration, well washed with cold water, then dried. Yield: 9.8 g Synthesis of intermediate (III):

A solution of 5.5 g of (II) obtained in the above-described step in 50 ml of ether was stirred by means of a magnetic stirrer. Separately, a mixed solution was prepared by adding 18 ml of N-(3-aminopropyl)-N-methyl-1,3-propane-diamine to 100 ml of ether. This mixed solution was added to the foregoing solution of (II), and the resulting mixture was stirred at room temperature for about one hour. The reaction was traced by silica gel chromatography. After completion of the reaction, 200 ml of water was added thereto, and the reaction solution was extracted twice with ethyl acetate, followed by washing the ethyl acetate layer with water. After drying the extract over magnesium sulfate, the solvent was distilled off under reduced pressure. The oily residue was used as such in the subsequent step without further purification.

Synthesis of Compound 5:

0.9 g of the oily residue obtained in the above-described step was dissolved in 30 ml of chloroform, 0.8 ml of triethylamine and 0.8 g of lauryl chloride were added thereto, and the resulting mixture was stirred for about 30 minutes. 50 ml of dilute hydrochloric acid was added to the reaction solution, followed by extracting the solution with choloroform. The chloroform layer was dried over magnesium sulfate, then the solvent was distilled off. The residue was purified by silica gel chromatography (chloroform : methanol $=20 : 1$) to obtain Compound 5 as a single spot. Yield: 1.1 g In the present invention, various conventional coating processes for forming a thin film may be employed for forming the water-insoluble organic thin film. As the coating process, coating solution applying processes (e.g., a spray coating process, a dip-coating process, a roller coating process, a spin-coating process), a chemical vapor deposition process, a vacuum deposition process, a sputtering process, and the like may be used but, in order to keep the precursor compound of the thin film component stable, coating solution-applying processes and chemical vapor deposition processes are preferred. Of the coating solution-applying processes, a spin-coating process is particularly preferred in view of forming a uniform film and reducing the thickness of the film. General descriptions of processes for forming thin films including the spin-coating process and the chemical vapor deposition process are given in Hakumaku Handbook (Thin Film Handbook), pp. 49 to 307, compiled by Nippon Gakujutsu Shinko-kai in 1983.

Solvents used for the spin-coating process, which vary depending upon the kind of the compound, include alkyl halides (e.g., dichloromethane, dichloroethane), aromatic compounds (e.g., toluene and xylene), ethers (e.g., methylcellosolve and ethylcellosolve), ketones (e.g., methyl ethyl ketone and cyclohexanone), esters (e.g., ethyl acetate and carbitol acetate), alcohols (e.g., ethanol and isopropyl alcohol) or the like. Upon coating, a dispersing agent, a storage stabilizer, a high molecular binder, a dye, a hardener, a thickening agent, etc. may also be used in combination with the precursor compound of the present invention.

The organic thin film comprising the precursor of the present invention preferably has a thickness of 50 Å to 10 μm, more preferably 100 Å to 5,000 Å, before immobilization of the bioactive protein.

The organic thin film of the present invention may contain various additives and binder materials and, after formation of the thin film, the precursor-containing thin film may be hardened by heating or irradiating with proper light. As the binder material, high molecular compounds, bioproteins such as gelatin, etc. may be used. These binders may be water-soluble but are required to become water-insoluble as a result of hardening.

As the hardener, dialdehydes, active vinyl-sulfones, triazine derivatives, etc. may be used.

In the present invention, chemical binding of a bioactive protein to the precursor-containing organic thin film can be attained by dipping the precursor thin film prepared in dark room or under safelight into an aqueous solution of a bioactive protein, or by forming a film of a bioactive protein on the precursor thin film using a coating solution-applying process or the like. At this time, the concentration of the bioactive protein solution is preferably from $10^{-6}$ to $10^3$M.

Those areas where a pattern is intended to be immobilized are then irradiated. The irradiation with light is conducted by using a proper band light of ultraviolet rays, a visible light, or a laser monochromatic light. The light preferably has a wavelength which is effective in the absorption range of the precursor of the present invention which includes a long wavelength region of the absorption range nearer the visible light region. When a xenon lamp of 100W is used as a light source, the irradiation period is preferably from 5 to 30 minutes.

The irradiation with light is preferably conducted in a low-temperature gas phase or liquid phase so as to minimize danger of damaging the bioactive protein. When the irradiation is conducted in a gas phase, the thin film having absorbed the protein in the solution is preferably exposed to light in an inert gas or under reduced pressure at $-20°$ C. to $5°$ C. When the irradiation is conducted in liquid phase, the thin film is preferably exposed at $0°$ C. to $5°$ C. after sufficiently absorbing the protein in the solution. However, heat may be applied upon irradiation with light for the purpose of promoting immobilization. The application of heat may be conducted by using infrared irradiation and preferably at $40°$ C. or less so is the protein is not deactivated.

The nitrene or carbene precursors to be used in the present invention may be those compounds which can undergo intermolecular polymerization reaction (monomer units of a high molecular compound), or the precursors themselves may be water-insoluble high molecular weight polymers, for example, high molecular weight compounds containing in its polymeric chain a reactive precursor moiety as described, e.g., in JP-B-49-23843, 46-43127, 51-3242 and 59-21013 and JP-A-51-59995 (The term "JP-B" used herein means an "examined Japanese patent publication").

As the support (base) to be used in the present invention for the functional organic thin film, various materials may be used such as conductors (e.g., various metals), glassy inorganic substances (e.g., glass and quartz) and other inorganic insulating substances, various inorganic and organic crystals, inorganic semiconductors (e.g., $SnO_2$, $In_2O_3$, $ZnO$, $TiO_2$, $WO_3$, GaAs and Si), organic semiconductors, organic conductors, organic polymers, and composite materials of these substances. The support may be an electrode or a transducer (e.g., sensor) capable of being connected to an external electric circuit. Examples of the transducer include semiconductor devices (such as silicon) and field effect transistors (FET). The surface of the support may be made hydrophilic or hydrophobic by various physical or chemical treatments. A preferable treatment for rendering the surface hydrophobic is to react an alkylsilane derivative as a coupling agent with the surface of the base.

In the structure of the thin film material of the present invention, molecules constituting the organic built-up film may be immobilized onto the surface of the base or support in contact with the organic film through chemical bonding. Such immobilization may be attained by heating or irradiation with electromagnetic beams to thereby promote the formation of chemical bonds between reactive groups on the base surface (e.g., hydroxy groups) and reactive groups of built-up film-constituting molecules (e.g., active silane or azide). For example, when gelatin containing amino groups are used as a binder, a difunctional silane such as glycidoxyalkoxysilane can be used as a binder for the surface of an oxide base.

Preferable examples of the bioactive proteins constituting the thin film of the present invention include enzymes, antigens, antibiotics. The enzymes include oxidases such as glucose oxidase, cholesterol oxidase, uricase and choline oxidase; dehydrogenases such as alcohol dehydrogenase, glycerol dehydrogenase, glucose-6-phosphoric acid dehydrogenase and glutamic acid dehydrogenase; and enzymes for analysis (peroxidase, urease, lipoprotein lipase, diaphorase, catalase, various kinases, and cholesterol esterase).

As the guest compounds such as antigen and antibody, there are illustrated many compounds including immunoglobulin G, etc. which are described in *Meneki no Kenkyu* (Studies on Immunity) compiled by Yuichi Yamamura and published by Dobun Shoin in 1986.

The thin film of the present invention comprising the precursor may be utilized in various fields such as sensor image formation, information recording, energy conversion, etc. by utilizing a chemical reaction (e.g., catalytic reaction, photochemical reaction and oxidation-reduction reaction) or a physical change (e.g., optical change and electric change) with high efficiency with an arbitrary functional compound (e.g., enzyme and protein) that is chemically immobilized onto the surface of the thin film. This arrangement utilizes the reactivity of the precursor, thus being extremely useful.

The present invention is now illustrated in more detail by reference to the following examples which, however, are not to be construed as limiting the present invention in any way. Unless otherwise indicated, all parts, percents and ratios are by weight.

EXAMPLE 1

A nitrene precursor, Compound 2, was dissolved in a mixed solvent of dichloromethane and ethanol to a concentration of 1% (w/v). The solution was spin-coated on a glass base (of which the surface had been made hydrophobic by treating with a toluene solution of stearyltrichlorosilane), under a dark red lamp using a spinner, then dried to form an uniform organic thin film about 200 Å thick. Measurement of the visible light absorption spectrum of the film using a spectrophotometer revealed a broad absorption having a maximum absorption at around 470 nm. The glass plate was dipped in pure water, then in 1 N NaCl each for 5 hours in a dark room at room temperature under stirring, and again subjected to measurement of visible light absorption spectrum. No reduction in absorption intensity was observed.

Then the base was dipped in a neutral aqueous solution containing $10^{-5}$ M of glucose oxidase (GOD) and, while cooling the solution to 0° C. using ice-water, the thin film on the surface of the base was continuously irradiated for 30 minutes with a 100W halide lamp (with filtering UV light). Similarly, a base dipped in the GOD solution but not irradiated with light was prepared. These bases were well rinsed successively with pure water and 1 N NaCl, then dipped in a buffer solution of 5.6 in pH containing 0.01 M of glucose to conduct an enzymatic reaction 37° C. for 30 minutes. After completion of the reaction, a solution of a mixture of peroxidase and ABTS (leuco dye colorant) was added as an indicator to the reaction solution, and the solution was stirred to determine $H_2O_2$ produced by oxidation of glucose. As a result, the GOD-immobilizing base irradiated with light was found to produce in a considerable amount, i.e., two times or more as much as that of the non-irradiated base. With the base sample onto which GOD was immobilized by irradiation with light (possibly by adsorption), production of $H_2O_2$ stopped after removal of the base sample from the reaction solution. This fact shows that GOD was not released from the base sample into the solution.

EXAMPLE 2

A carbene precursor, Compound 19, was dissolved in dichloroethane to a concentration of 1% (w/v), and coated on the surface of a flat gold plate having been made hydrophobic with trimethylchlorosilane, according to a spin-coating process to form an uniform organic thin film about 100 Å thick. The base was dipped in a neutral aqueous solution containing $10^{-6}$ M urease at 10° C. for 1 hour, then taken out and lightly rinsed with pure water. The base was then irradiated with light emitted from a 500W mercury lamp at room temperature for about 10 minutes. The base was again washed successively with water and 1 N NaCl, then dipped in an aqueous solution containing $10^{-3}$ M of urea at 30° C. for 30 minutes under stirring.

The reaction solution was subjected to a conventional colorimetric test using Nessler's reagent. As a result, a yellowing reaction was observed which demonstrated the production of ammonia. The color reaction was significantly greater in comparison with a similarly prepared base not having been irradiated with light.

While the present invention has been described in detail and with reference to specific embodiments thereof, it will be apparent to one skilled in the art that various changes and modifications can be made therein without departing from the spirit and the scope of the present invention.

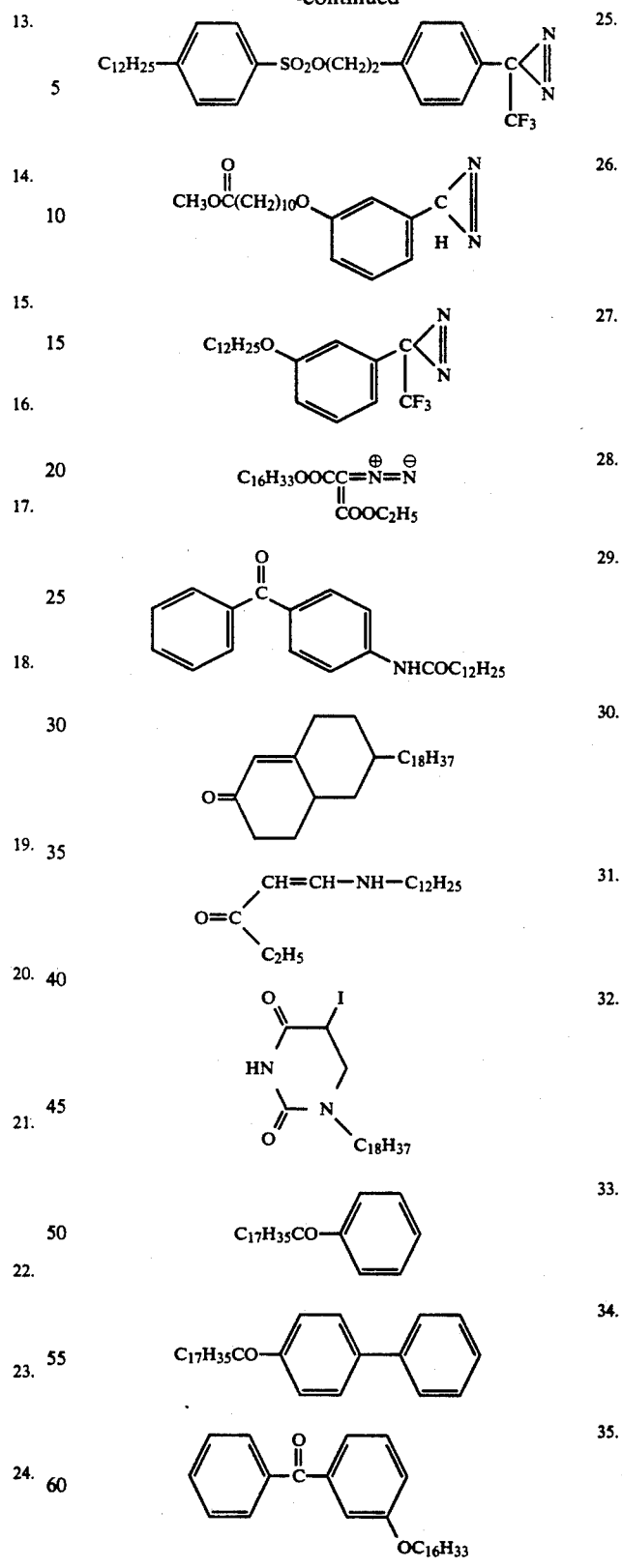

What is claimed is:

1. A method for producing a functional organic thin film material comprising the steps of:
   (a) forming a water insoluble organic thin film on a support;
   (b) coating on said water insoluble organic thin film by a casting method, a composition containing at least one precursor selected from a group consisting of a nitrene precursor and a carbene precursor;
   (c) depositing by absorption a bioactive protein on said water insoluble organic thin film; and
   (d) exposing said bioactive protein adsorbed on said water insoluble organic thin film to light.

2. A method according to claim 1, wherein said nitrene precursor is an azido compound or a diazido compound, and said carbene precursor is an α-diazoketone or an aryldiazirine compound.

3. A method according to claim 1, wherein said step of absorbing a bioactive protein is by dipping the water-insoluble organic thin film in an aqueous solution of the bioactive protein.

4. A method according to claim 1, wherein said water-insoluble organic thin film is from about 40 Å to about 10 μm thick.

5. A method according to claim 4, wherein said water-insoluble organic thin film is from about 100 to 5,000 Å thick.

6. A method according to claim 1, wherein said water-insoluble organic thin film further contains a binder.

7. A method according to claim 1, wherein said step of exposing said bioactive protein and said water-insoluble organic thin film to light is at a low temperature is in a gas phase or a liquid phase.

8. A method according to claim 1, wherein at least one of said at least on precursor is a polymerizale monomer.

9. A method according to claim 1, wherein at least one of said at least one precursor is a water-insoluble polymer.

10. A method according to claim 1, wherein step (a) of absorbing a bioactive protein on a water-insoluble organic thin film provided on a support comprises:
   coating a coating composition comprising a water-insoluble precursor and a binder on aid support.

11. A method according to claim 1, wherein said support is selected from he group consisting of conductors, glassy inorganic substances, other inorganic insulating substances, inorganic and organic crystals, inorganic semiconductors, organic semiconductors, organic conductors, organic polymers, and composite materials of these substances.

12. A method according to claim 1, wherein said support is selected from the group consisting of an electrode and a transducer.

13. A method according to claim 1, wherein said precursor is selected from the group consisting of the following compounds:

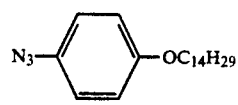
1.

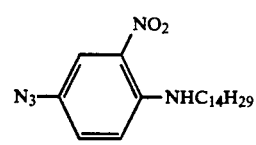
2.

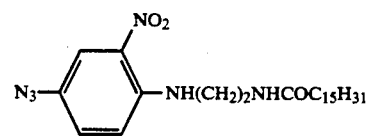
3.

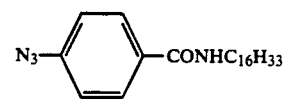
4.

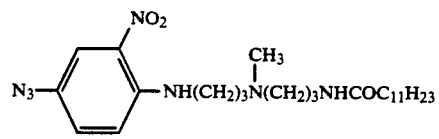
5.

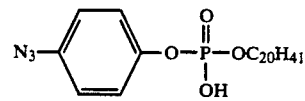
6.

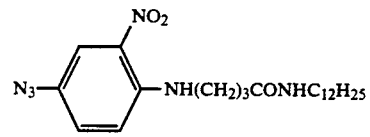
7.

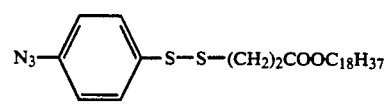
8.

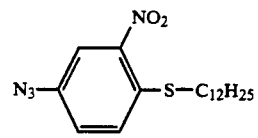
9.

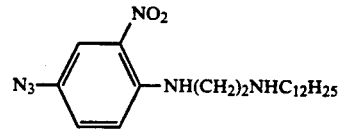
10.

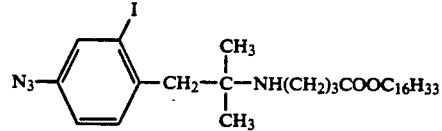
11.

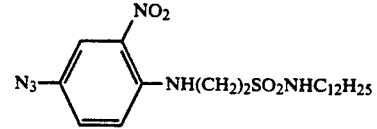
12.